United States Patent

Snell et al.

(10) Patent No.: US 8,834,497 B2
(45) Date of Patent: Sep. 16, 2014

(54) SUB-CORTICAL SUTURE CUTTER

(75) Inventors: Douglas B. Snell, Amesbury, MA (US); Daniel E. Morgan, Salem, MA (US)

(73) Assignee: Tornier, Inc., Bloomington, MN (US)

(*) Notice: Subject to any disclaimer, the term of this patent is extended or adjusted under 35 U.S.C. 154(b) by 715 days.

(21) Appl. No.: 13/149,214

(22) Filed: May 31, 2011

(65) Prior Publication Data

US 2012/0136378 A1 May 31, 2012

Related U.S. Application Data

(60) Provisional application No. 61/349,944, filed on May 31, 2010.

(30) Foreign Application Priority Data

Aug. 6, 2010 (EP) .................................. 10305866

(51) Int. Cl.
*A61B 17/04* (2006.01)
*A61B 17/29* (2006.01)

(52) U.S. Cl.
CPC ..... *A61B 17/0467* (2013.01); *A61B 2017/2911* (2013.01); *A61B 2017/0403* (2013.01)
USPC .......................................... 606/148; 606/167

(58) Field of Classification Search
CPC .................................................. A61B 17/0467
USPC ............ 606/138, 148, 167, 170; 112/169, 285
See application file for complete search history.

(56) References Cited

U.S. PATENT DOCUMENTS

| | | | | |
|---|---|---|---|---|
| 3,995,619 A * | 12/1976 | Glatzer | .......................... | 600/550 |
| 6,254,620 B1 * | 7/2001 | Koh et al. | ..................... | 606/167 |
| 7,879,055 B1 * | 2/2011 | Stone et al. | ................... | 606/170 |
| 2002/0087178 A1 * | 7/2002 | Nobles et al. | ................. | 606/167 |
| 2003/0078601 A1 * | 4/2003 | Shikhman et al. | ............ | 606/148 |
| 2003/0120287 A1 * | 6/2003 | Gross et al. | ................... | 606/148 |
| 2004/0122450 A1 * | 6/2004 | Oren et al. | .................... | 606/148 |
| 2004/0254598 A1 * | 12/2004 | Schumacher et al. | ........ | 606/170 |
| 2005/0059983 A1 * | 3/2005 | Opolski et al. | ................ | 606/148 |
| 2005/0234481 A1 * | 10/2005 | Waller | ........................ | 606/148 |
| 2006/0212045 A1 * | 9/2006 | Schilling et al. | .............. | 606/138 |
| 2006/0293700 A1 * | 12/2006 | Dana et al. | .................... | 606/148 |

(Continued)

FOREIGN PATENT DOCUMENTS

EP              2098171 A1    9/2009

*Primary Examiner* — Julian W Woo
*Assistant Examiner* — Shaun L David
(74) *Attorney, Agent, or Firm* — Knobbe Martens Olson & Bear, LLP

(57) ABSTRACT

An arthroscopic suture cutting device according to embodiments of the invention includes an outer tube; an inner rod including an outer surface and an aperture, a distalmost edge of a second distal opening located distally of a distalmost edge of a first distal opening, the inner rod can receive a suture extending through both distal openings; in a loading position, the inner rod extends distally of the outer tube to receive the suture; in an intermediate position, the distal openings are closer to the outer tube, such that the suture is permitted to slide through the aperture without release; and in a cut position, the distalmost edges of the distal openings are within the outer tube. Moving from intermediate position to cut position draws the suture between outer tube and inner rod, urging the inner rod radially toward the second distal opening, cutting the suture between the outer tube and the distalmost edge of the second distal opening.

21 Claims, 5 Drawing Sheets

(56) References Cited

U.S. PATENT DOCUMENTS

| | | |
|---|---|---|
| 2007/0106310 A1* | 5/2007 | Goldin et al. .................. 606/148 |
| 2007/0173865 A1* | 7/2007 | Oren et al. ..................... 606/148 |
| 2008/0228198 A1* | 9/2008 | Traynor et al. ................ 606/138 |
| 2009/0228026 A1* | 9/2009 | Koogle et al. ................. 606/148 |
| 2010/0049213 A1* | 2/2010 | Serina et al. ................... 606/139 |
| 2011/0313430 A1* | 12/2011 | Miller ........................... 606/138 |

* cited by examiner

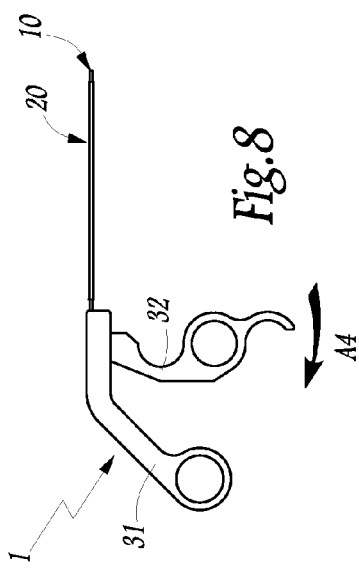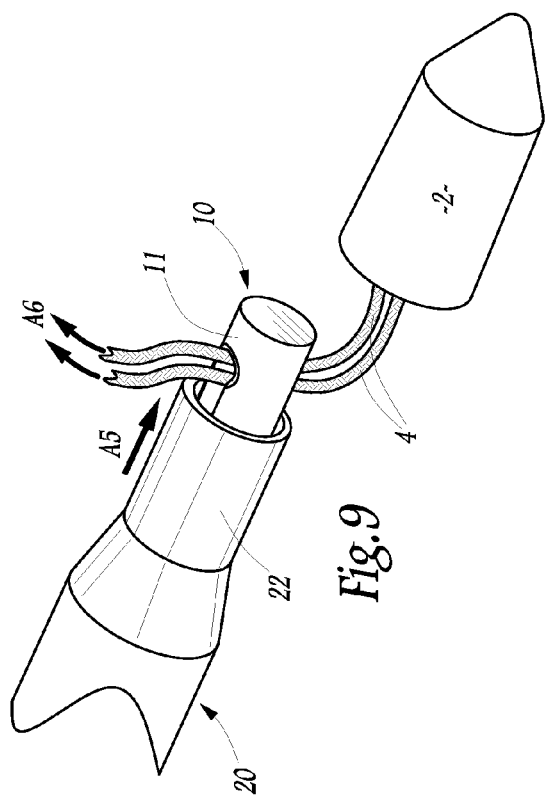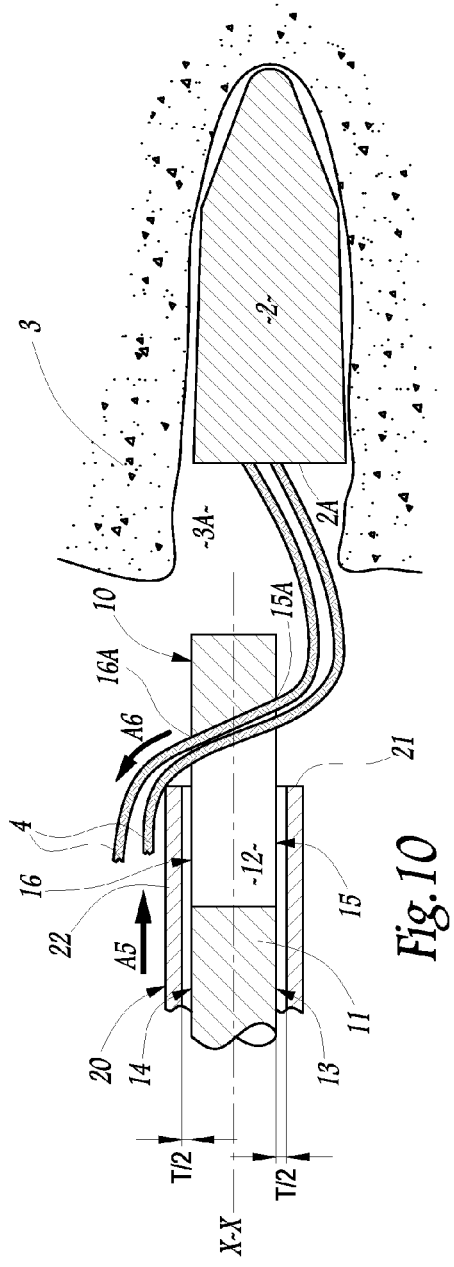

SUB-CORTICAL SUTURE CUTTER

CROSS-REFERENCE TO RELATED APPLICATIONS

This application claims the benefit of U.S. Provisional Patent Application Ser. No. 61/349,944, filed on May 31, 2010, and claims foreign priority to European Patent Application No. EP10305866.5, filed on Aug. 6, 2010, both of which are incorporated herein by reference in their entireties.

TECHNICAL FIELD

Embodiments of the present invention relate to an arthroscopic device and methods for cutting suture.

BACKGROUND

In arthroscopic surgical procedures, for example arthroscopic procedures in the joint space of a human shoulder, anchors are often implanted to secure a graft or a synthetic endoprosthesis, such as a patch, to a bone. To accomplish this, sutures are often fixedly connected to the anchors, after having been threaded through at least the graft or the endoprosthesis. At the end of the procedure, the free tails of these sutures need to be cut because they constitute foreign bodies in the joint space.

Existing arthroscopic devices for cutting suture typically require a high level of skill and dexterity, particularly in arthroscopic use, in order to avoid only partially cutting the sutures. Existing devices also typically leave a significant length of suture in place after cutting, which often protrude from a bone hole and present an abrasion material in the tightly spaced bone joint, and which can decrease the quality of the outcome of the arthroscopic procedure.

SUMMARY

Embodiments of the present invention include arthroscopic suture cutting devices which eliminate the free suture tails as far as possible, in a simple and efficient manner.

According to some embodiments of the present invention, a radial tolerance is provided between the inner member, which may also be referred to as an inner rod, and the outer body of the device, which may also be referred to as an outer tube, and a suture to be cut is threaded in a radial gap between one side of the inner member and the outer body, in order to induce a tension on the suture and to use the suture to bias the two components when they are moved into each other for cutting the suture. In this way, the cutter action may be performed with a zero or minimal clearance between the opposing side of the inner member and a facing portion of the outer body.

For the surgeon, embodiments of the present invention are easy to use and efficient. After having placed a suture to be cut in the distal hole of the inner member, the distal end part of this member is placed where the cutting is desired, for example as near as possible to the structure from which the suture protrudes, in particular as near as possible to a proximal end of a bone anchor from which the suture extends. Then, after having pulled on the suture to reduce its length between the device and the structure, the surgeon controls the device to move the outer body from its load position to its cut position. The suture is wedged between the inner and outer members of the device during operation in order to provide a zero or minimal clearance radial fit between the inner member and the outer body when these two components interfere for cutting the suture. After the cutting, the remaining part of the suture is as short as possible. In particular, the distal end part of the device is introduced in a bone hole for cutting a suture extending from this bone hole, below the bone surface. In other words, the device eliminates the suture tail from a bone joint space, according to embodiments of the present invention. As such, any distal geometry of the device, which fits inside a bone hole or a bone tunnel, may be employed.

A device for cutting suture arthroscopically according to embodiments of the present invention includes an outer tube having a distal end configured for arthroscopic insertion; an inner rod within the outer tube, the outer tube sliding longitudinally with respect to the inner rod, the inner rod comprising an outer surface and an aperture, the aperture comprising a first distal opening and a second distal opening, wherein a distalmost edge of the second distal opening is located distally of a distalmost edge of the first distal opening, wherein the outer surface at least partially separates the first and second distal openings, and wherein the inner rod is configured to receive a suture extending through the first and second distal openings. In a loading position, the inner rod extends distally of the distal end of the outer tube to permit the inner rod to receive the suture extending through the first and second distal openings. In an intermediate position, the first and second distal openings are closer to the distal end of the outer tube than in the loading position, such that the suture is permitted to slide through the aperture without being released by the aperture. In a cut position, the distalmost edges of the first and second distal openings are both within the outer tube, and the outer tube and the inner rod are arranged such that moving the inner rod and outer tube from the intermediate position to the cut position draws the suture between the outer tube and a portion of the inner rod distal to the distalmost edge of the first distal opening, thereby urging the inner rod at least partially in a radial direction toward the second distal opening, cutting the suture between the outer tube and the distalmost edge of the second distal opening at a location where the distalmost edge of the second distal opening meets the outer tube.

According to some embodiments of the present invention, a distal end of the inner rod is substantially cylindrical and comprises a longitudinal axis, and the distal end of the inner rod further includes a distal end face formed in a plane that is substantially perpendicular to the longitudinal axis. In some cases, the first distal opening may be radially opposed to the second distal opening. A distal end of the inner rod may be substantially cylindrical and include a longitudinal axis, and the first and second distal openings may be substantially aligned in a direction perpendicular to the longitudinal axis. According to some embodiments of the present invention, the aperture further comprises a proximal opening located proximally of the first and second distal openings, and in the loading position, at least a portion of the proximal opening extends distally of the distal end of the outer tube, and in the intermediate position, the proximal opening is entirely within the outer tube. The proximal opening may be configured to accept the suture into the aperture in a substantially radial direction.

The aperture formed in the inner rod may be peripherally delimited by a continuous wall. In some cases, the distalmost edge of the second distal opening includes a cutting edge. In other cases, the outer tube includes a cutting edge at the location where the distalmost edge of the second distal opening meets the outer tube. And in yet other cases, both the second distal opening and the outer tube comprise cutting edges. According to embodiments of the present invention, the inner rod does not rotate about its longitudinal axis with respect to the outer tube.

Embodiments of the present invention may further include a handle portion adapted to control movement of the outer tube with respect to the inner rod between the loading position, the intermediate position, and the cut position. The handle portion may further include a handle fixedly secured to a proximal end of the inner rod and an actuator movably coupled to the handle, such that movement of the actuator slides the outer tube with respect to the inner rod. Alternatively, the handle may be fixedly secured to a proximal end of the outer tube and an actuator movably coupled to the handle, such that movement of the actuator slides the inner rod with respect to the outer tube. Some embodiments of the present invention further include a suture, the width of the suture being substantially the same as the distance between the distalmost edge of the first distal opening and the outer tube in the cut position. Such embodiments may further include a suture anchor adapted to be implanted in bone and to which the suture is connected, and a maximum transversal dimension of the distal end of the outer tube may be smaller than a maximum transversal dimension of the suture anchor.

A method for cutting suture arthroscopically according to embodiments of the present invention includes inserting an outer tube and an inner rod arthroscopically, the inner rod within the outer tube, the outer tube having a distal end, the outer tube slidable longitudinally with respect to the inner rod, the inner rod comprising an outer surface and an aperture, the aperture including a first distal opening and a second distal opening, wherein a distalmost edge of the second distal opening is located distally of a distalmost edge of the first distal opening, and wherein the outer surface at least partially separates the first and second distal openings. The method may further include receiving a suture into the aperture, such that the suture extends through the first and second distal openings; moving the outer tube distally with respect to the inner rod until the distalmost edge of the first distal opening is within the outer tube and the suture is wedged between an inner surface of the outer tube and the outer surface of the inner rod distal of the distalmost edge of the first distal opening, thereby urging the inner rod at least partially in a radial direction toward the second distal opening; and moving the outer tube further distally with respect to the inner rod until the suture is cut between the outer tube and the distalmost edge of the second distal opening at a location where the distalmost edge of the second distal opening meets the outer tube.

According to some embodiments of the present invention, the aperture further includes a proximal opening located proximally of the first and second distal openings, and the method further includes moving the outer tube with respect to the inner rod to a position in which the suture slides freely within the aperture through the first and second distal openings, and in which the proximal opening is entirely within the outer tube. The suture may be connected to a suture anchor implanted into bone beneath a bone surface, and may be cut at a location leaving suture tails attached to the suture anchor that are shorter than a distance between the suture anchor and the bone surface, according to embodiments of the present invention. Receiving the suture into the aperture may include receiving the suture into the aperture in a substantially radial direction. The outer tube and the inner rod may be operably coupled with a handle portion adapted to control movement of the outer tube with respect to the inner rod, according to embodiments of the present invention. The handle portion may include a handle fixedly secured to a proximal end of the inner rod and an actuator movably coupled to the handle, such that moving the outer tube distally with respect to the inner rod comprises moving the actuator.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 8 illustrates an elevation view of the suture cutting device of FIG. 5 in an intermediate sliding position, according to embodiments of the present invention.

FIG. 9 illustrates a perspective view of a distal part of the suture cutting device of FIG. 8 in an intermediate sliding position, according to embodiments of the present invention.

FIG. 10 illustrates a sectional view of the distal part of FIG. 9 in the intermediate sliding position and a suture anchor implanted in bone, to which the suture is connected, according to embodiments of the present invention.

Figure 1:
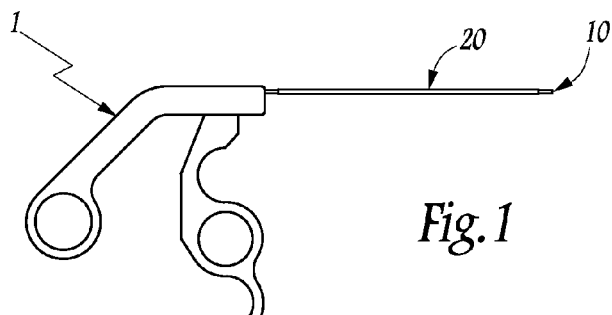
FIG. 1 illustrates an elevation view of a suture cutting device, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIGS. 1-4 depict an arthroscopic cutter device 1 including an inner rod 10 and an outer tube 20. Rod 10 extends in length about a central axis X-X. According to some embodiments, the rod 10 is cylindrical, with a circular base centered on axis X-X.

Figure 2:
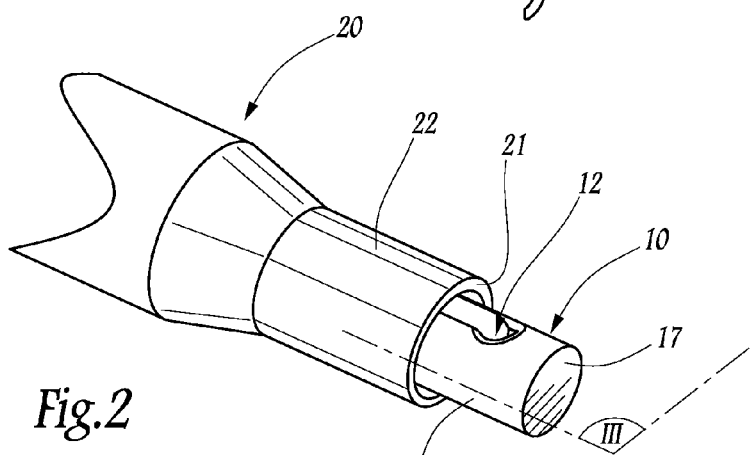
FIG. 2 illustrates a perspective view of a distal part of the suture cutting device of FIG. 1, according to embodiments of the present invention.
Figure 3:
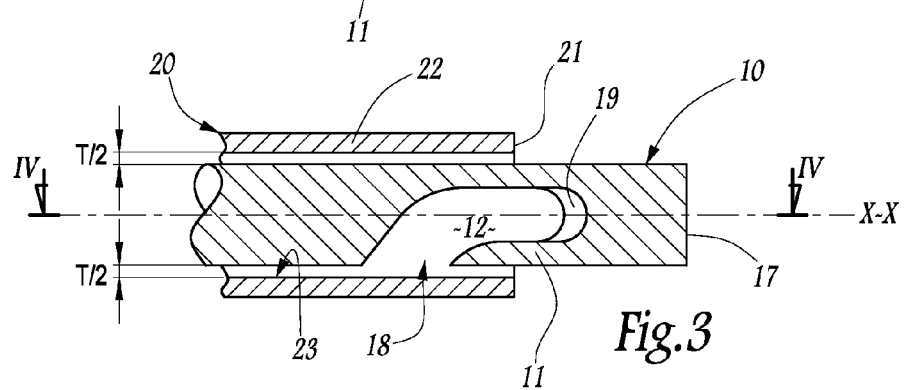
FIG. 3 illustrates a sectional view of the distal part of FIG. 2 taken along plane III of FIG. 2, according to embodiments of the present invention.
Figure 4:
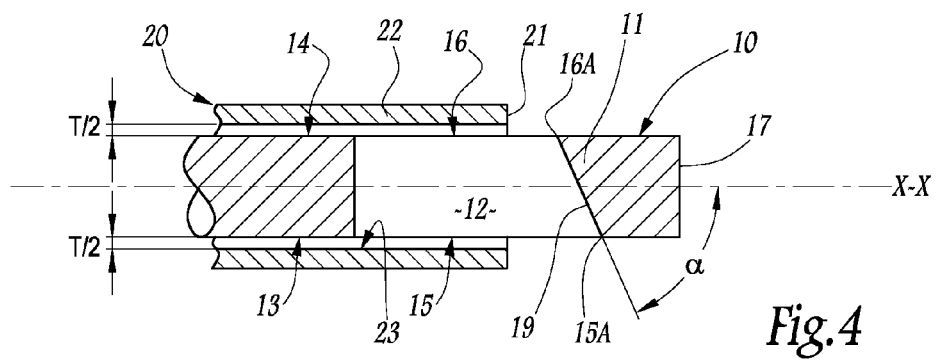
FIG. 4 illustrates a sectional view of the distal part of FIG. 3 taken along line IV-IV of FIG. 3, according to embodiments of the present invention.

Tube 20 is arranged around rod 10, extending along substantially all the length of the rod, except at a distal end part 11 of rod 10, which emerges from a distal end 21 of tube 20, as clearly shown in FIGS. 2-4. Tube 20 is substantially coaxial with rod 10 and has a cross section which internally corresponds to the cross section of rod 10. A non-zero radial tolerance T is formed between the tube 20 and rod 10. In FIGS. 3 and 4, this tolerance T is uniformly distributed around rod 10, such that half of tolerance T is located between the rod and each of the two radially opposed portions of tube 20 represented in section. According to some embodiments, tube 20 has a cross section which is both internally and externally tubular and/or circular.

In use, tube 20 moves axially around rod 10, by sliding. In this way, the distal end part 21 of tube 20 is able to cover a variable length of distal end part 11 of rod 10. In order to control the relative movement between rod 10 and tube 20, device 1 comprises a control system. A handle 31 is fixedly connected to a proximal part of rod 10, and a lever 32 is mounted in an articulated manner to this handle, so that, when rocked around an axis perpendicular to axis X-X, the lever transmits force and motion to tube 20 with respect to rod 10. In practice, different transmission mechanisms may be arranged between tube 20 and an actuator such as lever 32 to impart similar motion. In some embodiments of the present invention, the outer tube 20 is fixedly attached to the handle 1; in other embodiments, the rod 10 is fixedly attached to the handle 1.

The handle control system is adapted to be actuated outside a human body while a distal part of rod 10, including its end part 11, and a distal part of tube 20, including an end part 22 thereof, are placed in a bone joint space, after having been introduced via an arthroscopic cannula. The outside diameter of tube 20 may be dimensioned accordingly.

As illustrated in FIGS. 2-4, end part 11 of rod 10 is provided with a through hole 12 which extends transversally to axis X-X. Through hole 12 may also be referred to as an aperture 12. This hole 12 extends between two radially opposed sides 13 and 14 of rod 10, joining two free openings 15 and 16 delimited by rod 10, respectively on side 13 and on side 14 thereof. Openings 15 and 16 may also be referred to as distal openings 15, 16. As shown in FIG. 4, opening 15 presents a distalmost edge 15A which is nearer to the distal end 17 of rod 10 than the distalmost edge 16A of opening 16. In other words, the line extending through the aforesaid two distal end points 15A and 16A is not perpendicular to axis X-X, but defines with respect to this axis X-X an angle α different from 90°. In this way, insofar as distal end 21 of tube 20 lies in a geometrical plane perpendicular to axis X-X, when the tube 20 is axially moved about rod 10 in direction toward distal end 17 of the rod, end part 22 of the tube progressively overlaps the openings 15 and 16, but covers in totality opening 16 before covering in totality opening 15, because, along axis X-X, its end 21 radially faces end point 16A before radially facing end point 15A.

End part 11 of rod 10 is shaped in the form of a J-hook: in addition to its two opposed openings 15 and 16, hole 12 is also open on one of the two sides which link to each other side 13 and 14 around rod 10. In other words, as shown in FIG. 3, hole 12 is peripherally delimited by a wall the distal portion 19 of which joints the openings 15 and 16, the proximal portion of which is broken by an opening 18 which is defined in one of the aforesaid two sides of rod 10, distinctively from the openings 15 and 16. In order to obtain the J-shape, this opening 18 is axially offset with respect to the openings 15 and 16, being situated further from distal end 17 of rod 10 than these openings 15 and 16.

An example of the use of device 1 will be now explained. In a first step, when device 1 is at rest as shown in FIGS. 1 to 4, the distal parts of rod 10 and tube 20 are introduced in a bone joint space, for example in a glenohumeral space of a human shoulder. Before the suture cutting procedure, an arthroscopic surgical procedure may have been performed, for example during which a bone anchor was implanted in one of the bones defining the joint space, this bone anchor and the aforesaid bone being respectively referenced 2 and 3 on FIGS. 10, 11 and 14. The proximal end 2A of anchor 2 is below the surface of bone 3, which keeps free a sub-cortical volume 3A in bone 3, corresponding to the proximal part of the hole where anchor 2 is implanted. Anchor 2 is non-removably connected to two sutures 4 shown in FIGS. 6 and 7. In practice, the connection between the anchor and these sutures 4 may be achieved in different ways: for example, each of these sutures may be locked by a locking mechanism integrated in the anchor, or may be pinched between the external face of the anchor and the wall of the bone hole in which the anchor is implanted, according to embodiments of the present invention.

Figure 5:
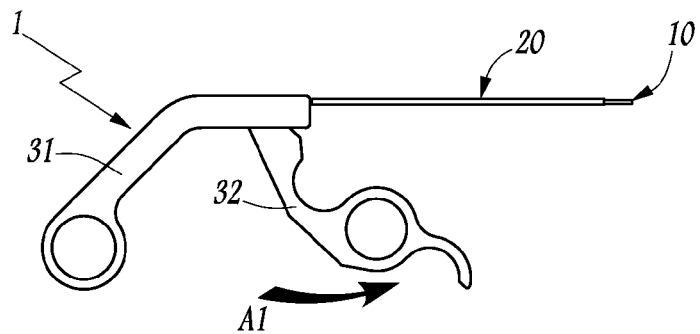
FIG. 5 illustrates an elevation view of the suture cutting device, in a loading position, according to embodiments of the present invention.
Figure 6:
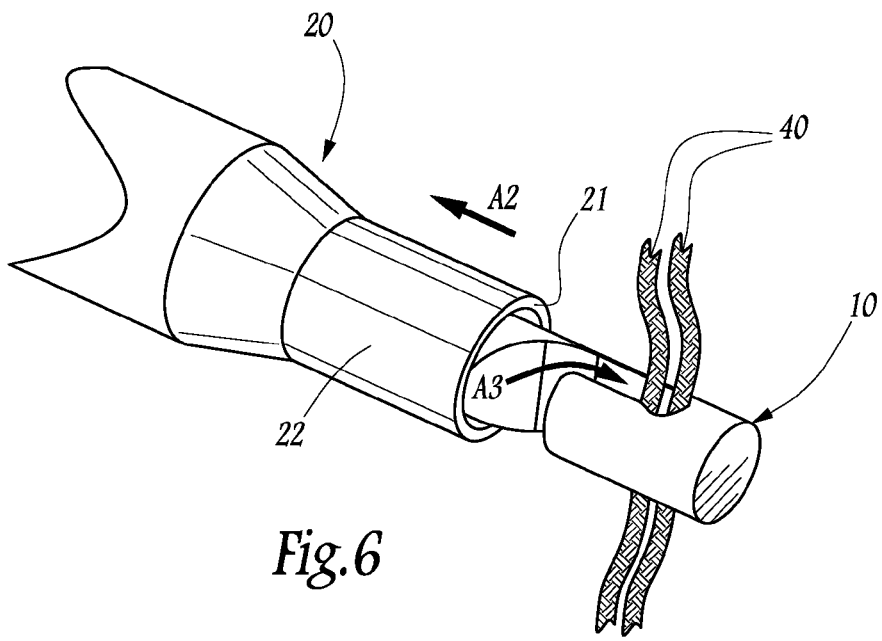
FIG. 6 illustrates a perspective view of the distal part of the suture cutting device of FIG. 5 in the loading position, according to embodiments of the present invention.
Figure 7:
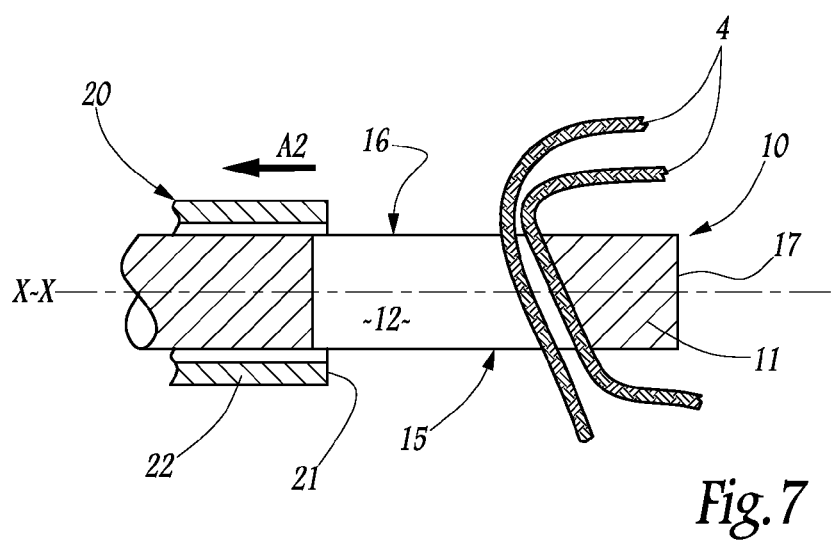
FIG. 7 illustrates a sectional view of the distal part of FIG. 6, similar to the view of FIG. 4, in the loading position, according to embodiments of the present invention.

In a second step shown in FIGS. 5 to 7, the surgeon moves lever 32 opposite of handle 31, as indicated by an arrow A1 in FIG. 5. In this way, tube 20 is driven in a proximal direction around rod 10, as indicated by an arrow A2 in FIGS. 6 and 7. Thus, tube 10 is moved from its rest position of FIGS. 1 to 4, in which end part 22 of the tube 10 covers the opening 18, to a load position shown in FIGS. 5 to 7, in which end part 22 reveals opening 18. In this way, hole 12 is free to receive the one or more sutures 4 which are advantageously introduced within hole 12 through opening 18 then axially driven to the distal portion 19 of hole 12, for example to the bottom of the J-shape of end part 11 of rod 10, as indicated by an arrow A3 in FIG. 6.

Of course, in the loading position, distal end 21 of tube 10 is sufficiently axially away from hole 12 to keep free the two main opposed openings 15 and 16 of hole 12. Alternatively, the J-hook shape of end part 11 of rod 10 may be replaced by an eyelet shape (not shown), in which, in end part 11 of rod 10, a continuous wall may peripherally delimit a hole similar to hole 12, which is open only at two opposed openings similar to the openings 15 and 16. In such a case, sutures 4 are threaded in this eyelet hole, according to embodiments of the present invention.

In a third step shown in FIGS. 8 to 11, the surgeon moves lever 32 towards handle 31, as indicated by an arrow A4 in FIG. 8. In this way, tube 20 is driven axially around rod 10 in a distal direction, as indicated by an arrow A5 in FIGS. 9 to 11. Thus, tube 20 moves from its loading position shown in FIGS. 5 to 7 to an intermediate position shown in FIGS. 8 to 10, in which end part 22 of the tube progressively covers the openings 15 and 16. In the same step, the surgeon moves device 1 nearer to bone anchor 2, for example by substantially aligning distal end 17 of rod 10 with subcortical volume 3A. The surgeon may progressively pull on sutures 4, as indicated by an arrow A6 in FIGS. 9 and 10, in order to progressively increase the length of the part of the sutures protruding from opening 16, which reduces to a similar extent the length of the parts of the sutures extending from anchor 2 to opening 15, according to embodiments of the present invention.

In the intermediate position of tube 20 and rod 10, the sutures 4 do not interfere with the tube 20, in the sense that, even if end part 22 of tube 20 covers in part the openings 15 and 16, distal end 21 of the tube is sufficiently separated in a proximal direction from the distal end points 15A and 16A of these openings to allow the sutures 4 to extend within hole 12, from side 13 of rod 10 to side 14 of this rod, without contacting the inner face 23 of tube 20. As shown in FIG. 10, radial tolerance T between rod 10 and tube 20 is distributed in a uniform manner around the rod, typically by half on side 13 and half on side 14. However, when tube 20 continues its distal sliding around rod 10 due to the movement of lever 32 towards handle 31, the tube reaches a subsequent pre-cutting position shown in FIG. 11. In this pre-cutting position of FIG. 11, distal end 21 of tube 20 is distally offset with respect to distal end point 16A of opening 16 along axis X-X; in other words, along this axis, distal end 21 is nearer to distal end 17 of rod 10 than distal end point 16A of opening 16. End part 22 of tube 20 axially covers the whole opening 16. At the same time, opening 15 is still partly open, because distal end 21 of tube 20 is proximally offset with respect to distal end point 15A of opening 15. In the pre-cutting position of FIG. 11, the arrangement of the sutures 4 through opening 15 is unchanged with respect to FIG. 10. However, on side 14 of rod 10 in FIG. 11, the path of the sutures 4 is modified because the sutures 4 need to go around distal end 21 of tube 20. For this purpose, the part of each suture 4, emerging from opening 16, slips radially between end part 11 of rod 10 and end part 22 of tube 20, that is to say slips into a radial gap 24 defined between inner face 23 of end part 22 of the tube and side 14 of end part 11 of the rod. Of course, this radial gap 24 is due to the radial tolerance T provided between rod 10 and tube 20.

Figure 11:
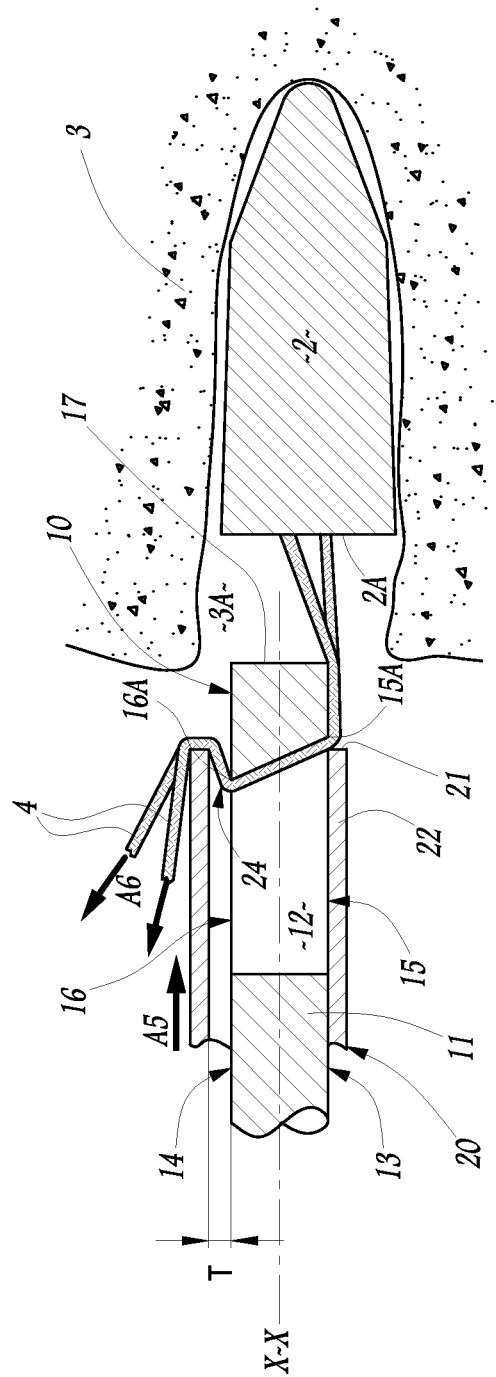
FIG. 11 illustrates a sectional view similar to FIG. 10, showing a relative movement between the sutures and the components of the device in its slide configuration, just prior to entering the cut position, according to embodiments of the present invention.

In practice, one of ordinary skill in the art will understand, based on the present disclosure, that when tube 20 is moved from its position of FIG. 10 to its position of FIG. 11, the sutures 4 induce a biasing action between rod 10 and tube 20. Indeed, when distal end 21 of tube 20 is very near to distal end point 16A of opening 16, the suture part axially interposed, or wedged, between them tends to control a transversal movement of tube 20 with respect to rod 10, according to which, on side 14 of rod 10, inner face 23 of the tube radially moves away from the rod whereas, on side 13 of rod 10, inner face 23 of the tube radially moves closer to the rod. Due to the strength of the sutures 4 and/or the fact that these sutures are sufficiently tightened by the surgeon, the part of the sutures passing through gap 24 radially enlarges this gap as much as possible, until the radial dimension of this gap corresponds to the total value of tolerance T, as shown in FIG. 11. In this way, on side 13 of rod 10, inner face 23 of the tube contacts the rod without radial clearance, or with minimal radial clearance.

Figure 13:
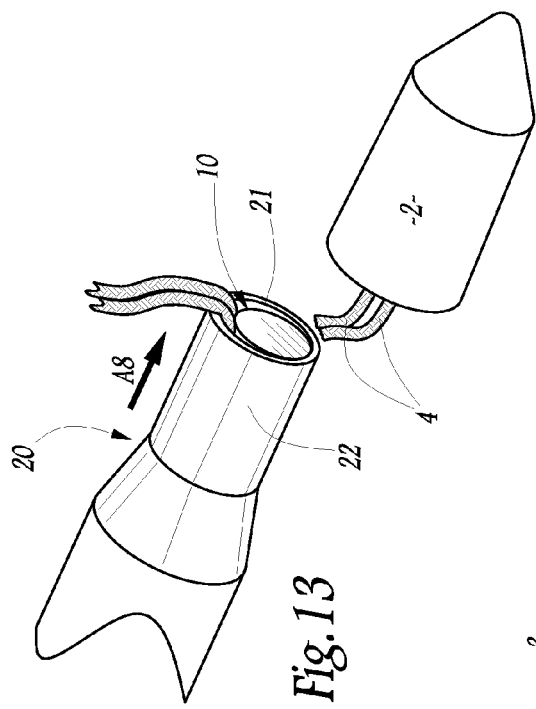
FIG. 13 illustrates a perspective view of a distal part of the suture cutting device of FIG. 12 in the cut position, according to embodiments of the present invention.
Figure 12:
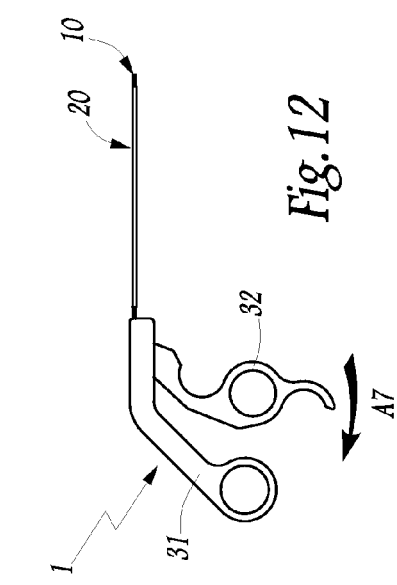
FIG. 12 illustrates an elevation view of the suture cutting device of FIG. 8 in a cut position, according to embodiments of the present invention.
Figure 14:
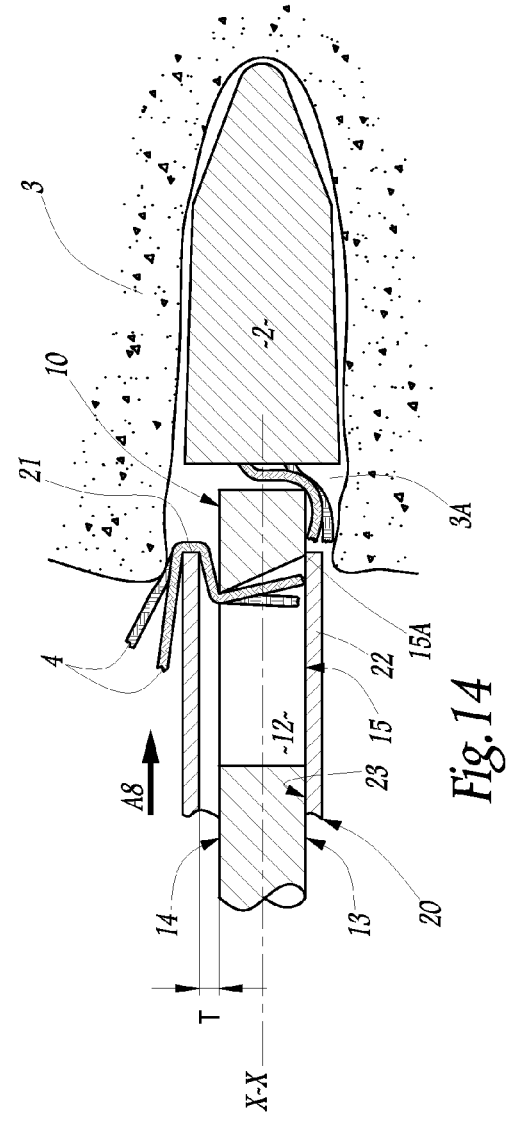
FIG. 14 illustrates a sectional view similar to FIG. 11, showing the suture cutting device in the cut position and cut suture tails, according to embodiments of the present invention.

In a fourth step, as the surgeon continues to move lever 32 towards handle 31 as indicated by an arrow A7 in FIG. 12, tube 20 continues to be axially moved in a distal direction, as indicated by an arrow A8 in FIGS. 13 and 14, and reaches a cut position shown in FIGS. 12 to 14. In this cut position, end part 22 of tube 20 axially covers the whole opening 15, such that distal end 21 of tube 20 axially reaches distal end point 15A of opening 15. As inner face 23 of tube 20 contacts side 13 of hole 10 without clearance or with minimal clearance, the portion of distal end 21 of the tube, radially facing distal end point 15A of opening 15, interferes with this end point, with interposition of the sutures 4 which are cut by this mechanical interference between rod 10 and tube 20. This cutting action may be performed by a cutting edge located at distal end point 15A of opening 15, more generally located in a distal portion of this opening 15. Another solution includes arranging a cutting edge in the portion of distal end 21 of tube 20, which radially faces side 13 of rod 10. Tube 10 may be fixed in rotation around axis X-X with respect to rod 10, according to embodiments of the present invention. Two cutting edges may be provided respectively at opening 15 and at distal end 21 of tube, according to embodiments of the present invention.

The biasing action provided by the sutures 4 may be adjusted with an appropriate gauging of device 1. In particular, the tolerance T and angle α may be chosen so that the non-cutting side 14 of rod 10 engages tube 20 before the cutting side 13 does, in order to ensure that the tolerance T is removed from the rod and the tube at this side 13. According to embodiments of the present invention, the device 1 is calibrated for cutting ultra high molecular weight polyethylene (UHMWPE) suture.

The surgeon drives tube 20 up to its cut position, after having put in place distal end 17 of rod 10 at the desired location, and/or nearest as possible to anchor 2, for example after having introduced distal end 21 of tube 20 within subcortical volume 3A delimited in bone 3 where anchor 2 is implanted, as shown in FIG. 14. According to embodiments of the present invention, the outside diameter of tube 20 is lower than the diameter of the bone hole in which anchor 2 is implanted, permitting introduction of the tube below the surface of bone 3; the outside diameter of the tube may be lower than the maximal outside diameter of anchor 2.

According to one alternative embodiment (not shown), the relative arrangement between distal end 21 of tube 20 and distal portion 19 of hole 12 is reversed: rather than, as in the embodiment shown in FIGS. 1 to 14, distal end 21 of tube 20 lying perpendicularly to axis X-X and the distal end points 15A and 16A of the openings 15 and 16 being offset along this axis, the two radially opposed openings of the hole provided in the distal end part of the rod may be aligned, with the distal portion of this hole extending perpendicularly to the axis of the rod, if the two portions of the distal end part of the tube, respectively facing the two opposed sides of the rod where these openings are formed, have respective distal end points which are offset with respect to each other along the axis of the rod.

Although inner rod 10 is described in some embodiments as being cylindrical and having a longitudinal axis, one of ordinary skill in the art, based on the disclosure provided herein, will appreciate that rod 10 may take any number of uniform and non-uniform cross-sectional shapes along its length. And although outer tube 20 is described in some embodiments as being tubular and/or cylindrical, one of ordinary skill in the art, based on the disclosure provided herein, will appreciate that outer tube 20 may take any number of uniform and non-uniform cross-sectional shapes along its length, including without limitation a tubular shape which is not a closed tubular shape, and/or which is open along some percentage of its circumference at certain longitudinal locations.

Because the device 1 is configured to cut suture between the distalmost edge 15A and the very outer edge 21 of the outer tube 22, the device 1 is capable of receiving the suture 40 and being slid lower and further (e.g. closer to the bottom ends of the sutures attached to a countersunk bone anchor 2) than conventional suture cutters, which require enough suture length to gather and cut the suture on a surface interior to the device. This need for extra slack between the cutter and the suture anchor in conventional suture cutting devices often leaves suture tails that are too long and which protrude above the bone surface into which the suture anchor is implanted. Device 1, on the other hand, can cut suture below the cortical surface, according to embodiments of the present invention.

A device 1 for cutting suture arthroscopically according to embodiments of the present invention includes an outer tube 20 having a distal end 21 configured for arthroscopic insertion; an inner rod 10 within the outer tube 20, the outer tube 20 sliding longitudinally with respect to inner rod 10, the inner rod 10 including an outer surface and an aperture 12, the aperture 12 including a first distal opening 16 and a second distal opening 15, wherein a distalmost edge 15A of the second distal opening 15 is located distally of a distalmost edge 16A of the first distal opening 16, wherein the outer surface at least partially separates the first 16 and second 15 distal openings, and wherein the inner rod 10 is configured to receive a suture 40 extending through the first and second distal openings 15, 16. In a loading position (as illustrated in FIGS. 5-7), the distal end 11 of inner rod 10 extends distally of the distal end 21 of the outer tube 20 to permit the inner rod 10 to receive the suture 40 extending through the first and second distal openings 15, 16. In an intermediate position, (as illustrated in FIGS. 8-10), the first and second distal openings 15, 16 are closer to the distal end 21 of the outer tube 20 than in the loading position, such that the suture 40 is permitted to slide through the aperture 12 without being released by the aperture 12. In a cut position (as illustrated in FIGS. 12-14), the distalmost edges of the first and second distal openings are both within the outer tube 20, and the outer tube 20 and the inner rod 10 are arranged such that moving the inner rod 10 and outer tube 20 from the intermediate position (e.g. of FIG. 10) to the cut position (e.g. of FIG. 14) draws the suture 10 between the outer tube 20 and a portion of the inner rod 10 distal to the distalmost edge 16A of the first distal opening 16, thereby urging the inner rod 10 at least partially in a radial direction toward the second distal opening 15, cutting the suture 40 between the outer tube 20 and the distalmost edge 15A of the second distal opening 15 at a location where the distalmost edge 15A of the second distal opening 15 meets the outer tube 20.

According to some embodiments of the present invention, a distal end 11 of the inner rod 10 is substantially cylindrical (see, for example, FIG. 2) and comprises a longitudinal axis X-X, and the distal end 11 of the inner rod 10 further includes a distal end face 17 formed in a plane that is substantially perpendicular to the longitudinal axis X-X. In some cases, the first distal opening 16 may be radially opposed to the second distal opening 15. A distal end 11 of the inner rod 10 may be substantially cylindrical and include a longitudinal axis X-X, and the first and second distal openings 15, 16 may be substantially aligned in a direction perpendicular to the longitudinal axis X-X. According to some embodiments of the present invention, the aperture 12 further includes a proximal opening 18 located proximally of the first and second distal openings 15, 16, and in the loading position (see FIG. 6), at least a portion of the proximal opening 18 extends distally of the distal end 21 of the outer tube 20, and in the intermediate position (see FIG. 9), the proximal opening 18 is entirely within the outer tube 20. The proximal opening 18 may be configured to accept the suture 40 into the aperture 12 in a substantially radial direction, as indicated by arrow A3.

The aperture 12 formed in the inner rod 10 may be peripherally delimited by a continuous wall (see FIGS. 3 and 4). In some cases, the distalmost edge 15A of the second distal opening 15 includes a cutting edge. In other cases, the outer tube 20 includes a cutting edge at the location where the distalmost edge 15A of the second distal opening 15 meets the outer tube 20. And in yet other cases, both the second distal opening 15 and the outer tube 20 comprise cutting edges. According to embodiments of the present invention, the inner rod 10 does not rotate about its longitudinal axis X-X with respect to the outer tube 20.

Embodiments of the present invention may further include a handle portion adapted to control movement of the outer tube 20 with respect to the inner rod 10 between the loading position, the intermediate position, and the cut position. The handle portion may further include a handle 31 fixedly secured to a proximal end of the inner rod 10 and an actuator 32 movably coupled to the handle 31, such that movement of the actuator 32 slides the outer tube 20 with respect to the inner rod 10. Alternatively, the handle portion may further include a handle 31 fixedly secured to a proximal end of the outer tube 20 and an actuator 32 movably coupled to the handle 31, such that movement of the actuator 32 slides the inner rod 10 with respect to the outer tube 20. According to yet other embodiments, the inner rod 10 and outer tube 20 are coupled in a way which permits relative longitudinal movement between inner rod 10 and outer tube 20 by sliding both inner rod 10 and outer tube 20. Some embodiments of the present invention further include a suture 40, the width of the suture 40 being substantially the same as the distance T between the distalmost edge 16A of the first distal opening 16 and the outer tube 20 in the cut position (see FIG. 14). Such embodiments may further include a suture anchor 2 adapted to be implanted in bone 3 and to which the suture 40 is connected, and a maximum transversal dimension of the distal end 21 of the outer tube 20 may be smaller than a maximum transversal dimension of the suture anchor 2.

A method for cutting suture arthroscopically according to embodiments of the present invention includes inserting an outer tube 20 and an inner rod 10 arthroscopically, the outer tube 20 having a distal end 21, the inner rod 10 within the outer tube 20, the outer tube 20 slidable longitudinally with respect to the inner rod 10, the inner rod 10 comprising an outer surface and an aperture 12, the aperture 12 including a first distal opening 16 and a second distal opening 15, wherein a distalmost edge 15A of the second distal opening 15 is located distally of a distalmost edge 16A of the first distal opening 16, and wherein the outer surface at least partially separates the first and second distal openings 15, 16. The method may further include receiving a suture 40 into the aperture 12, for example along the direction indicated by arrow A3, such that the suture 40 extends through the first and second distal openings 15, 16 (see FIG. 6); moving the outer tube 20 distally with respect to the inner rod 10 until the distalmost edge 16A of the first distal opening 16 is within the outer tube 20 and the suture 40 is wedged between an inner surface of the outer tube 20 and the outer surface of the inner rod 10 distal of the distalmost edge 16A of the first distal opening 16, thereby urging the inner rod 10 at least partially in a radial direction toward the second distal opening 15; and moving the outer tube 20 further distally with respect to the inner rod 10 until the suture 40 is cut between the outer tube 20 and the distalmost edge 15A of the second distal opening 15 at a location where the distalmost edge 15A of the second distal opening 15 meets the outer tube 20.

According to some embodiments of the present invention, the aperture 12 further includes a proximal opening 18 located proximally of the first and second distal openings 15, 16, and the method further includes moving the outer tube 20 with respect to the inner rod 10 to a position in which the suture 40 slides freely within the aperture 12 through the first and second distal openings 15, 16 (see FIG. 9) and in which the proximal opening 18 is entirely within the outer tube 20. The suture 40 may be connected to a suture anchor 2 implanted into bone 3 beneath a bone surface, and may be cut at a location leaving suture tails attached to the suture anchor 2 that are shorter than a distance between the suture anchor 2 and the bone surface (see FIG. 14), according to embodiments of the present invention. Receiving the suture 40 into the aperture 12 may include receiving the suture 40 into the aperture 12 in a substantially radial direction, as indicated by arrow A3, according to embodiments of the present invention. The outer tube 20 and the inner rod 10 may be operably coupled with a handle portion adapted to control movement of the outer tube 20 with respect to the inner rod 10, according to embodiments of the present invention. The handle portion may include a handle 31 fixedly secured to a proximal end of the inner rod 10 and an actuator 32 movably coupled to the handle 31, such that moving the outer tube 20 distally with respect to the inner rod 10 comprises moving the actuator 32.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A device for cutting suture arthroscopically, the device comprising:
   an outer tube having a distal end configured for arthroscopic insertion;
   an inner rod within the outer tube, wherein the outer tube slides longitudinally with respect to the inner rod, the inner rod comprising an outer surface and an aperture, the aperture comprising a first distal opening and a second distal opening, wherein a distalmost edge of the second distal opening is located distally of a distalmost edge of the first distal opening, wherein the outer surface at least partially separates the first and second distal openings, and wherein the inner rod is configured to receive a suture extending through the first and second distal openings;
   wherein in a loading position, the inner rod extends distally of the distal end of the outer tube to permit the inner rod to receive the suture extending through the first and second distal openings;
   wherein in an intermediate position, the first and second distal openings are closer to the distal end of the outer tube than in the loading position, such that the suture is permitted to slide through the aperture without being released by the aperture; and
   wherein in a cut position, the distalmost edges of the first and second distal openings are both within the outer tube, and wherein the outer tube and the inner rod are arranged such that moving the inner rod and outer tube from the intermediate position to the cut position draws the suture between the outer tube and a portion of the inner rod distal to the distalmost edge of the first distal opening, thereby urging the inner rod at least partially in a radial direction toward the second distal opening, cutting the suture between the outer tube and the distalmost edge of the second distal opening at a location where the distalmost edge of the second distal opening meets the outer tube.

2. The device of claim 1, wherein a distal end of the inner rod is substantially cylindrical and comprises a longitudinal axis, and wherein the distal end of the inner rod further comprises a distal end face formed in a plane that is substantially perpendicular to the longitudinal axis.

3. The device of claim 1, wherein the first distal opening is radially opposed to the second distal opening.

4. The device of claim 1, wherein a distal end of the inner rod is substantially cylindrical and comprises a longitudinal axis, and wherein the first and second distal openings are substantially aligned in a direction perpendicular to the longitudinal axis.

5. The device of claim 1, wherein the aperture further comprises a proximal opening located proximally of the first and second distal openings, wherein in the loading position, at least a portion of the proximal opening extends distally of the distal end of the outer tube, and wherein in the intermediate position, the proximal opening is entirely within the outer tube.

6. The device of claim 5, wherein the proximal opening is configured to accept the suture into the aperture in a substantially radial direction.

7. The device of claim 5, wherein the aperture is peripherally delimited by a continuous wall.

8. The device of claim 1, wherein the distalmost edge of the second distal opening comprises a cutting edge.

9. The device of claim 1, wherein the outer tube comprises a cutting edge at the location where the distalmost edge of the second distal opening meets the outer tube.

10. The device of claim 1, wherein the inner rod does not rotate about its longitudinal axis with respect to the outer tube.

11. The device of claim 1, further comprising a handle portion adapted to control movement of the outer tube with respect to the inner rod between the loading position, the intermediate position, and the cut position.

12. The device of claim 11, wherein the handle portion further comprises a handle fixedly secured to a proximal end of the inner rod and an actuator movably coupled to the handle, such that movement of the actuator slides the outer tube with respect to the inner rod.

13. The device of claim 11, wherein the handle portion further comprises a handle fixedly secured to a proximal end of the outer tube and an actuator movably coupled to the handle, such that movement of the actuator slides the inner rod with respect to the outer tube.

14. The device of claim 1, further comprising the suture, wherein a width of the suture is substantially the same as a distance between the distalmost edge of the first distal opening and the outer tube in the cut position.

15. The device of claim 14, further comprising a suture anchor adapted to be implanted in bone and to which the suture is connected, wherein a maximum transversal dimension of the distal end of the outer tube is smaller than a maximum transversal dimension of the suture anchor.

16. A method for cutting suture arthroscopically, the method comprising:
   inserting an outer tube and an inner rod arthroscopically, the outer tube having a distal end, the inner rod within the outer tube, the outer tube slidable longitudinally with respect to the inner rod, the inner rod comprising an outer surface and an aperture, the aperture comprising a first distal opening and a second distal opening, wherein a distalmost edge of the second distal opening is located distally of a distalmost edge of the first distal opening, wherein the outer surface at least partially separates the first and second distal openings;
   receiving a suture into the aperture, such that the suture extends through the first and second distal openings;

moving the outer tube distally with respect to the inner rod until the distalmost edge of the first distal opening is within the outer tube and the suture is wedged between an inner surface of the outer tube and the outer surface of the inner rod distal of the distalmost edge of the first distal opening, thereby urging the inner rod at least partially in a radial direction toward the second distal opening; and moving the outer tube further distally with respect to the inner rod until the suture is cut between the outer tube and the distalmost edge of the second distal opening at a location where the distalmost edge of the second distal opening meets the outer tube.

17. The method of claim 16, wherein the aperture further comprises a proximal opening located proximally of the first and second distal openings, the method further comprising moving the outer tube with respect to the inner rod to a position in which the suture slides freely within the aperture through the first and second distal openings, and in which the proximal opening is entirely within the outer tube.

18. The method of claim 16, wherein the suture is connected to a suture anchor implanted into bone beneath a bone surface, and wherein the suture is cut at a location leaving suture tails attached to the suture anchor that are shorter than a distance between the suture anchor and the bone surface.

19. The method of claim 16, wherein receiving the suture into the aperture comprises receiving the suture into the aperture in a substantially radial direction.

20. The method of claim 16, wherein the outer tube and the inner rod are operably coupled with a handle portion adapted to control movement of the outer tube with respect to the inner rod.

21. The method of claim 20, wherein the handle portion comprises a handle fixedly secured to a proximal end of the inner rod and an actuator movably coupled to the handle, wherein moving the outer tube distally with respect to the inner rod comprises moving the actuator.

* * * * *